(12) United States Patent
Ranganathan

(10) Patent No.: US 8,257,750 B2
(45) Date of Patent: Sep. 4, 2012

(54) CALCIUM CARBONATE COMPOSITIONS FOR PREVENTING OR TREATING HYPERPHOSPHATEMIA

(75) Inventor: Natarajan Ranganathan, Broomall, PA (US)

(73) Assignee: Kibow Biotech, Inc., Newtown Square, PA (US)

( * ) Notice: Subject to any disclaimer, the term of this patent is extended or adjusted under 35 U.S.C. 154(b) by 957 days.

(21) Appl. No.: 12/182,254

(22) Filed: Jul. 30, 2008

(65) Prior Publication Data

US 2009/0004297 A1   Jan. 1, 2009

Related U.S. Application Data

(63) Continuation-in-part of application No. 11/279,159, filed on Apr. 10, 2006, now Pat. No. 7,998,470.

(51) Int. Cl.
*A61K 33/06* (2006.01)
*A61K 33/10* (2006.01)

(52) U.S. Cl. .................................. 424/682; 424/687

(58) Field of Classification Search .............. 424/682, 424/687
See application file for complete search history.

(56) References Cited

U.S. PATENT DOCUMENTS 5,744,479 A * 4/1998 Furuya et al. ............. 514/301
2010/0098774 A1 * 4/2010 Ben et al. .................. 424/538

FOREIGN PATENT DOCUMENTS

DE      2749506 A   * 11/1977
WO   WO 2008/041236   *  4/2008

OTHER PUBLICATIONS

Ittel et al., "Calcium carbonate as a phosphate binder in dialysis patients:evaluation of an enteric-coated preparation and effect of additional aluminum hydroxide on hyperaluminaemia", Klin Wochenschr 1991 69:59-67.
Asher et al., "Projections and measurements of in vivo performance of liquid membrane capsules", Kidney Int. 1976 10:S254-S258.
Chang, T.M.S., "Artificial Cells, Chapter 5, in Biomedical Applications of Microencapsulation" edited by Lim, F. CRC Press Florida, pp. 86-100.
Sparks, R.E., "Gastrosorbents in the therapy of uremia:Inferences from intestinal loop dialysis", Kidney Int. 1975 Suppl 7:S373-S376.
Yatzidis et al., "Newer oral sorbents in uremia", Clinical Nephrology 1979 11:105-106.
Goldenhersh et al., "Effect of microencapsulation on competitive absorption in intestinal fluids", Kidney Int. 1976 10:S251-S253.
Kolff, W.J., "Longitudinal perspective on sorbents in uremia", Kidney Int. 1976 10:S211-S214.
Okada et al., "Correction by oral absorbent of abnormal digestive tract milieu in rats with chronic renal failure", Nephrol. Dial. Transplant 1995 10(5):671-676.

* cited by examiner

*Primary Examiner* — Ruth Davis
(74) *Attorney, Agent, or Firm* — Licata & Tyrrell P.C.

(57) ABSTRACT

Compositions and methods for inhibiting gastrointestinal absorption of phosphate in a subject are provided. Such compositions are composed of enteric-coated, sustained-release calcium carbonate, which find application in the prevention or treatment of hyperphosphatemia.

6 Claims, 1 Drawing Sheet

CALCIUM CARBONATE COMPOSITIONS FOR PREVENTING OR TREATING HYPERPHOSPHATEMIA

CROSS REFERENCE TO RELATED APPLICATIONS

This application is a continuation-in-part of U.S. patent application Ser. No. 11/279,159, filed Apr. 10, 2006 now U.S. Pat. No. 7,998,470, which claims benefit from U.S. patent application Ser. No. 09/557,011, filed Apr. 20, 2000, now U.S. Pat. No. 6,706,263, and U.S. Provisional Patent Application Ser. No. 60/131,774, filed Apr. 30, 1999.

BACKGROUND OF THE INVENTION

Hyperphosphatemia is an electrolyte disturbance in which there is an abnormally elevated level of phosphate in the blood. Hyperphosphatemia can be caused by hypoparathyroidism due to the lack of PTH (parathyroid hormone), which has the effect of inhibiting renal reabsorption of phosphate. It is also commonly seen in chronic renal failure and caused by taking oral sodium phosphate solutions prescribed for bowel preparation for colonoscopy in children. Without effective treatment, hyperphosphatemia can lead to renal osteodystrophy, a collection of bone diseases characterized by bone pain, brittle bones, skeletal deformities and fractures.

The absorption of phosphate within the intestines has been investigated using in vivo triple lumen intestinal perfusion (Walton & Gray (1979) *Clin. Sci.* (*Lond*). 56(5):407-12). It has been found that phosphate is absorbed mostly in the jejunum, due not to pH differences, but to the larger pore size in its mucosa than in the ileum. The endogenous absorption of phosphate in the jejunal region via perfusion of phosphate-free solutions was found to be 20 μmol/30 minutes/40 cm. The transport of the phosphate occurs across the brush border of the jejunum via a sodium-phosphate co-transport system.

In a double-blind crossover study of 21 kidney failure patients receiving hemodialysis, it was shown that enteric-coated (targeted release in the small intestine) compared to gastric-coated (targeted release in acidic pH of the stomach) calcium carbonate allowed for higher doses without the possible risk of hypercalcemia (Ittel, et al. (1991) *Klin. Wochenschr.* 69(2):59-67). During the 6 month study, patients failed to develop hypercalcemia (defined as >2.75 mmol/l) when administered 3.1-3.6 g of enteric-coated $CaCO_3$ phosphate binder per day, unlike during the administration of gastric-coated $CaCO_3$.

Phosphate binders commercially available for treatment of hyperphosphatemia include PhosLo® (Calcium Acetate), Fosrenol® (Lanthanum Carbonate), and Renagel® (Sevelamer HCl). However, the inefficiency of commonly used phosphorus binders creates a clinical dilemma. The dose of the binder must be increased to control hyperphosphatemia, but increased risk of toxicity or other undesirable side affects of the binder results from the increased dose. This toxicity may include bone disease and aluminum dementia from aluminum-containing antacids and hypercalcemia and soft tissue calcification from calcium-containing antacids. These risks are particularly problematic in patients with chronic renal disease.

SUMMARY OF THE INVENTION

The present invention is a composition comprising or consisting of enteric-coated, sustained-release calcium carbonate. In particular embodiments, the calcium carbonate is microcrystalline calcium carbonate. Methods for using such compositions for providing sustained-release of calcium carbonate in the small intestine of a subject, inhibiting gastrointestinal absorption of phosphate or for preventing or treating hyperphosphatemia are also provided.

DETAILED DESCRIPTION OF THE INVENTION

Figure 1A:
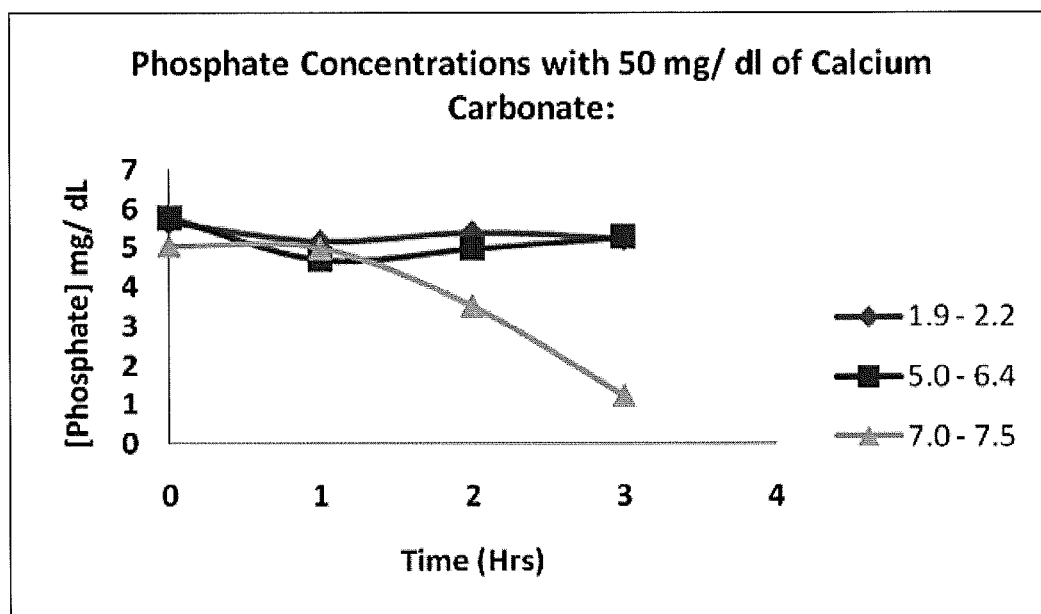
FIG. 1 shows pH-dependence of phosphate removal by 50 mg/dl (FIG. 1A) and 100 mg/dl (FIG. 1B) of calcium carbonate.

The invention relates to compositions and a method of controlling serum phosphate levels in subjects suffering from renal failure and associated hyperphosphatemia or subjects predisposed to development of a hyperphosphatemic condition. The composition of the present invention is composed of calcium carbonate which has been enteric-coated and microencapsulated to provide sustained-release of the calcium carbonate in the small intestine. In so far as the calcium carbonate is delivered in high quantities to the small intestine and released over a period of time, undesirable toxic side affects of calcium carbonate are minimized. Advantageously, continuous dispersion and bioavailability of calcium carbonate during digestion will also offer phosphate binding capabilities in the large colon.

The enteric-coated, sustained-release calcium carbonate composition of the invention is formulated as a therapeutic dosage form for oral administration to a subject afflicted with hyperphosphatemia or predisposed to develop that condition. Thus, the calcium carbonate is formulated as a unitary solid dosage form such as a compressed tablet, pill, or capsule. Methods and excipients for preparation of such dosage forms are well-known in the art.

The oral dosage form should be formulated to contain an effective amount of calcium carbonate compound to bind, upon ingestion by the subject, sufficient ingested phosphate in the subject's intestinal tract to inhibit the absorption of ingested phosphate and thereby reduce the probability of either the development of a hyperphosphatemic condition or the complication of an already existing hyperphosphatemic condition. Thus, each oral dose of the therapeutic calcium carbonate composition in accordance with this invention can contain from about 400 mg to about 1500 mg of calcium as calcium carbonate. An effective amount of the calcium carbonate composition to be administered will depend on the severity of the subject's condition, the nature of the subject's diet and the binding capacity of the calcium carbonate used in the formulation. By "effective amount" is meant an amount effective to achieve a selected desired result in accordance with the present invention, without undue adverse physiological effects or side effects; the desired result generally being a clinically observable reduction in absorption of ingested phosphate. The dosages of the compounds to be administered in accordance with this invention can thus be altered, if necessary, to correspond to the level of phosphate binding required in the subject's digestive tract. A daily dosage of about 400 mg to about 1500 mg of calcium as calcium carbonate is expected to be effective. Theoretically, according to the calculations based on molecular weight, 7.9 mg/dl of calcium carbonate is needed to remove 5 mg of phosphate. However, preliminary in vitro studies show that two daily doses of 500 mg of sustained-release $CaCO_3$ may be sufficient to remove 2.5 g of ingested dietary phosphate in the human gastrointestinal tract. However, this dosage depends on the subject and may vary accordingly.

Sustained- and continuous-release of calcium carbonate throughout the small and large intestine can be achieved using any conventionally employed microencapsulation process in the pharmaceutical arts. Microencapsulation is defined herein as the process of surrounding or enveloping one substance within another substance so that the core material is released either gradually through the capsule walls via controlled release or diffusion, or via a trigger from the external environment which melts or dissolves the capsule wall. Exemplary microencapsulation materials include, but are not limited to, biodegradable polymers such as ethylcellulose, hydroxypropyl methylcellulose, water-soluble polyamino acid, albumin, gelatin, collagen, fibrinogen, polylactides (PLA), polyglycolides (PGA), poly (lactide-co-glycolide)s (PLGA), polyethylene glycol (PEG), poly .beta.-hydroxy butyric acid (PHB), polycaprolactone, polyanhydrides, polyorthoesters, polyurethanes, poly(butyric acid)s, poly(valeric acid)s, poly(lactide-co-caprolactone) and derivatives thereof, and copolymers thereof. By way of illustration, a sustained-release preparation of the present invention can be manufactured by dispersing calcium carbonate in a solvent containing a biodegradable polymer and subjecting the resulting dispersion to formulation. Methods for microencapsulation of therapeutic compounds are disclosed, e.g., in U.S. Pat. Nos. 6,953,593 and 5,362,424, incorporated herein by reference in their entireties.

In accordance with this invention, the microencapsulated calcium carbonate is also enteric-coated to allow the calcium carbonate to be delivered to the small intestine. In so far as calcium carbonate will form calcium chloride as it reacts with the high levels of HCl in the stomach (pH 1.5-4.0), bypass of the stomach is essential to delivering high levels of calcium carbonate to the target site, i.e., the small intestine. Indeed, in-vitro data has shown that phosphate binding efficiency for calcium carbonate reaches 99% in 2 hours as compared to 28.6% in 5 hours for calcium chloride. Thus, formation of calcium chloride reduces the phosphate binding efficiency by 70.4% as compared to calcium carbonate. Accordingly, to optimize both the amount of calcium carbonate reaching the small intestine and deliver the calcium carbonate to the site of phosphate absorption into the blood stream, enteric-coating of the calcium carbonate is employed. Desirably, enteric-coating is achieved via a material that disintegrates and dissolves at a pH of 7.0 or higher (e.g., pH 7.0-8.5) then slowly disperses and traverses through the intestinal track over a period of approximately 8-12 hours thereby providing optimal phosphate binding in the small intestine. Examples of enteric coatings with these characteristics include, but are not limited to, Zein, polyglycolactic acid, polylactic acid, polylactide-co-glycolide and similar coating materials. Enteric coatings also enable delivery of sorbents to their site of action in relatively native form without binding of various digestive materials to the sorbents prior to reaching the target region.

In particular embodiments of the present invention, the solubility of the calcium carbonate is increased under the physiological conditions of the gastrointestinal tract (i.e., a pH between 7.0 and 8.5) by employing a microcrystalline calcium carbonate, e.g., with a mean particle diameter from about 0.01 micron up to 10 micron. The mean diameter of a microcrystalline calcium carbonate particle is the maximum dimension of a straight line passing through the center of the particle. Microcrystalline calcium carbonate ranging from about 0.2 micron and larger can be obtained commercially in dry form.

In addition to calcium carbonate, some embodiments of the present invention embrace adding other binding agents to the composition of the invention. For example, water binding agents such as psyllium fibers, naturally occurring gums or modified starches can be used in combination with the calcium carbonate of the instant composition.

The methods in accordance with this invention involve the administration, to a subject in need of treatment, the enteric-coated, sustained-release calcium carbonate composition disclosed herein. Therapeutic benefit can be realized in accordance with such methods by administering the composition orally to a subject to bind ingested phosphate in the subject's digestive tract, and thereby prevent intestinal absorption. In this regard, the instant composition provides a preventive and/or therapeutic treatment for hyperphosphatemia. Moreover, administration of the composition of the invention is expected to have a preventive and/or therapeutic effect toward a renal function disorder, chronic renal failure, dialysis, hypocalcemia, excess secretion of parathyroid hormone (PTH), suppression of vitamin D activation, ectopic calcification or the like wherein hyperphosphatemia is considered to be the cause of disease. Further, prevention or treatment of hyperphosphatemia in accordance with the present invention is expected to exert a remarkable preventive effect and/or therapeutic effect toward PTH increase due to hyperphosphatemia, secondary hyperparathyroidism via vitamin D lowering, renal osteodystrophy, uremia, central and peripheral nerve disorders, anemia, myocardial disorders, hyperlipemia, saccharometabolism disorders, itch, dermal ischemic ulcer, tendon rupture, reproductive dysfunction, muscle disorder, growth retardation, cardiac conduction disorders, alveolar diffusion disorders, arteriosclerosis, immunodeficiency, etc.

The present invention is further illustrated by the following non-limiting examples.

Example 1

Comparison of Mono- and Dibasic Potassium Phosphate

Monobasic potassium phosphate ($KH_2PO_4$) was used in all in vitro studies as a source of phosphate ions. This was compared to dibasic potassium phosphate ($K_2HPO_4$) to determine whether binding of phosphate by $CaCO_3$ was affected by the choice of phosphate source. Tribasic potassium phosphate was not considered as it dissociates in three steps at $pka_1$ of 2.12, $pKa_2$ of 7.21, and $pKa_3$ of 12.67, wherein only the first two steps need to be considered under physiological conditions Six 100 ml DI water systems containing 5 mg/dl of phosphate were prepared. Analytical grade $KH_2PO_4$ was used as a phosphate source for a set of three systems, and analytical grade $K_2HPO_4$ for a set of the remaining three systems (Sigma Chemical Co., St. Louis, Mo.). Then, 100 mg of $CaCO_3$ was added to all systems and pH was adjusted to 3.0, 7.0, and 8.0 for each set, using HCl. All systems were incubated in a shaker at 37° C. and 190 revolutions per minute (rpm) for 4 hours. Hourly, 1 ml samples were taken from each system and centrifuged in a microcentrifuge for three minutes. Each sample was then diluted 100× for measurement within the detectable range required by BIOASSAY Systems. In addition, pH was also measured hourly using a handheld waterproof "pHTestr" from Eutech Instruments. After 4 hours, all samples were analyzed for phosphate concentration using the malachite green phosphate assay kit (BIOASSAY Systems, Hayward, Calif.). All samples were measured for absorbance at the 650 nm wavelength using a JASCO spectrophotometer V-530. The absorbance values were then translated into phosphate concentration values.

The two forms of potassium phosphate were found to be almost equivalent at all three pH values and $CaCO_3$ failed to bind phosphate at pH 3.0. After 2 hours at pH 7.0, $CaCO_3$ bound phosphate more efficiently in the $K_2HPO_4$ system (99%) than in the $KH_2PO_4$ system (80%). However, 100% of phosphate was bound in all systems by the third hour. After 2 hours at pH 8.0, 94% of phosphate was bound in the $K_2HPO_4$ system versus 49% in the $KH_2PO_4$ system. This difference decreased after 3 hours (100% vs. 89%, respectively) and disappeared by the fourth hour.

Accordingly, $CaCO_3$ showed almost equivalent phosphate binding capacity with both forms of potassium phosphate. Therefore, the choice of the phosphate source is inconsequential. Thus, monobasic potassium phosphate was used in in vitro experiments.

Example 2

Effect of pH on Phosphate Binding

This in vitro investigation was performed to demonstrate the effect of pH on the phosphate binding capacity of calcium, using calcium carbonate as the phosphate binder and monobasic potassium phosphate as the phosphate source.

Six 100 ml DI water systems containing 5 mg/dl of phosphate were prepared. Analytical grade $KH_2PO_4$ was used as a phosphate source (Sigma Chemical Co., St. Louis, Mo.). Then, 50 mg of $CaCO_3$ was added to a set of three systems and 100 mg of $CaCO_3$ to a set of the remaining three systems. For each set, pH was adjusted to 3.0, 5.0, and 7.0 using HCl. All systems were incubated in a shaker at 37° C. and 190 revolutions per minute (rpm) for 3 hours. Hourly, 1 ml samples were taken from each system and centrifuged in a microcentrifuge for three minutes. Each sample was then diluted 100× for measurement within the detectable range required by BIOASSAY Systems. In addition, pH was also measured hourly using a handheld waterproof "pHTestr" from Eutech Instruments. After 3 hours, all samples were analyzed for phosphate concentration using the malachite green phosphate assay kit (BIOASSAY Systems, Hayward, Calif.). All samples were measured for absorbance at the 650 nm wavelength using a JASCO spectrophotometer V-530. The absorbance values were then translated into phosphate concentration values.

Figure 1B:
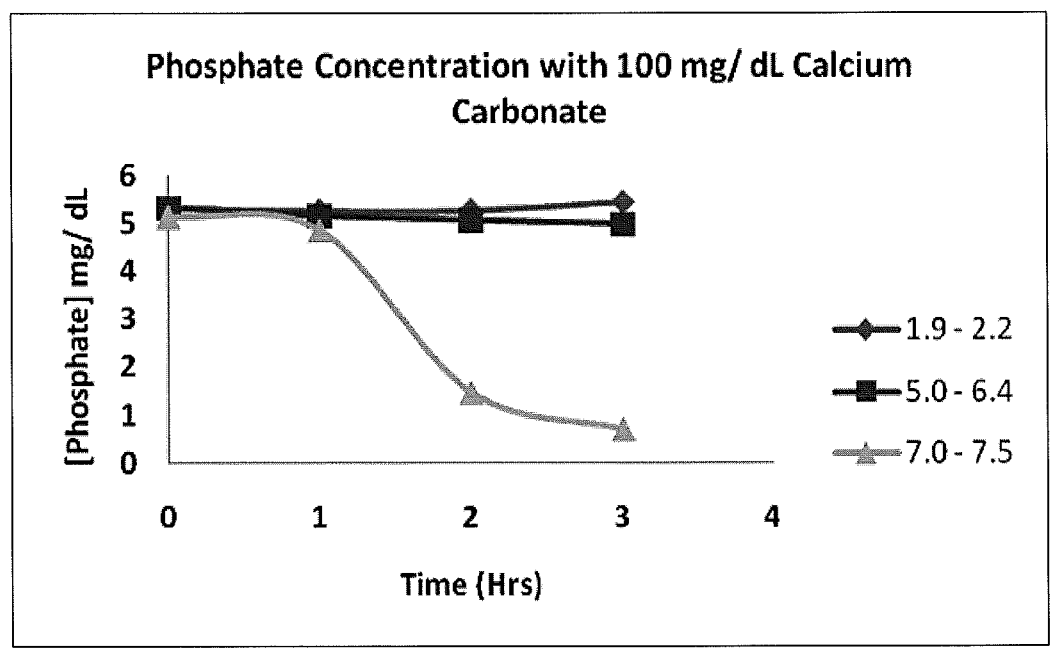

Addition of calcium carbonate significantly reduced phosphate levels at pH 7.0-7.5, but failed to do so at more acidic pH levels. At pH 7.0, the concentration of phosphate started decreasing after the first hour. A higher concentration of calcium carbonate led to a more rapid decrease in the concentrations of free phosphates. For example, after 2 hours at pH 7.0 the 50 mg system showed a reduction of 1.57 mg/dl, compared to 3.64 mg/dl in the 100 mg system. By the third hour, the phosphate concentration in the former system was reduced to 1.224 mg/dl and in the latter to 0.692 mg/dl (See FIGS. 1A and 1B).

These data indicate that calcium ions bound effectively to free phosphate in a pH-dependent fashion. The optimal pH range for calcium to bind to phosphate from $KH_2PO_4$ was between 7.0-7.5. These findings indicate that the formation of calcium chloride in acidic pH, such as the pH found in the stomach.

Example 3

In Vitro Comparison of Phosphate Binders

A series of in vitro experiments were performed to compare the efficacy of commonly used phosphate binders at different pH levels. The major phosphate binders currently on the market are calcium acetate (PhosLo®), lanthanum carbonate (Fosrenol®), sevelamer HCl (Renagel®) and, to a lesser extent, calcium carbonate.

Four 100 ml DI water systems were prepared in sterile disposable containers, each containing 5 mg/dl of phosphate. One system was for control, while 100 mg of $CaCO_3$ was added to each of the remaining three systems. Then, pH levels were adjusted to 3.0, 7.0 and 8.0. All four systems were incubated in a shaker at 37° C. and 190 rpm for 4 hours. Every 30 minutes, samples were taken and pH was adjusted. Each sample was diluted 100× for measurement using the malachite green phosphate assay kit (BIOASSAY Systems, Hayward, Calif.). All samples were measured for absorbance at the 650 nm wavelength using a JASCO spectrophotometer V-530. The absorbance values were then translated into phosphate concentration values. The same procedure was repeated for calcium acetate, lanthanum carbonate and sevelamer HCl.

These results indicated that $CaCO_3$ failed to bind at pH 3, likely due to formation of calcium chloride complex, as in the acidic stomach environment. However, it displayed optimal binding capacity at pH 7.0 and 8.0, binding phosphate more efficiently and rapidly than either calcium acetate or lanthanum carbonate. At pH 7.0, $CaCO_3$ removed 99% of phosphate within 2 hours and 100% within 3 hours. Similarly, at pH 8.0 $CaCO_3$ removed 96% in 2 hours and 100% in 3 hours. By comparison, pH of 3.0 was optimal for lanthanum carbonate. Phosphate levels were reduced from 6.252 mg/dl to 1.516 mg/dl (76% reduction) after 3 hours and to 0.873 mg/dl (86% reduction) after 4 hours. At pH 7 and 8, approximately 1 mg/dl reduction was shown after 4 hours. Calcium acetate failed to show any reduction in phosphate concentrations at any pH. The experiment was repeated twice to confirm these findings. Finally, sevelamer HCl displayed 100% phosphate binding within the first hour at all three pH levels.

These findings indicate that sevelamer is the most effective phosphate binder in vitro due to its spaced polycationic (mono-, di- and trivalent cations) polymeric structure, which allows binding at all pH. Lanthanum carbonate seemed to be only effective at low acidic pH levels, typically the environment of the stomach, while calcium carbonate was most effective at pH 7.0 and 8.0. Calcium acetate failed to induce any significant phosphate reduction. This was unexpected because clinical studies have shown that calcium acetate is equivalent to $CaCO_3$ in its phosphate-binding capacity, and both are comparable to sevelamer in terms of clinical outcomes. These in vitro findings were likely caused by the buffering effect of the acetate ions. The reported poor patient tolerability of calcium acetate may be partially attributed to this and other similar effects of the acetate salt in the GI tract.

Example 4

In Vivo Analysis of Sustained-Release Enteric-Coated Calcium Carbonate

A double-blind human clinical study will be conducted to compare the phosphate-binding capability of sustained-release enteric-coated versus non-coated calcium carbonate. The anticipated result is demonstration of the increased efficacy of sustained-release enteric-coated calcium carbonate form to reduce phosphate absorption at a lower dosage than non-coated calcium carbonate.

The objective is to release calcium carbonate within the duodenum of the small intestines, which maintains a pH between 7.0 and 8.5. Enteric coating is expected to begin rapid dissolution at pH 7.0 thereby releasing calcium carbonate between the duodenum region and the jejunum. Enteric-coating will be carried out using methacrylic acid copolymers, referred to as EUDRAGIT. There are four main types of chemical compositions for the EUDRAGIT polymers (i.e., methacrylic acid/ethyl acrylate copolymer; methacrylic acid: methyl methacrylate copolymer 50:50; methacrylic acid/methyl methacrylate 30:70; and methacrylic acid/methyl acrylate/methyl methacrylate), which are sustained-release to dissolve at specific pH levels. For the target delivery within the duodenum, a mix of EUDRAGIT L and EUDRAGIT S will be employed to release calcium carbonate at pH 7.0.

Clinical trials will be initiated by a two-month treatment period, followed immediately by a second two-month treatment period. This design allows for testing of both forms of calcium carbonate with patients serving as their own controls. Subjects will be evaluated for serum phosphate and calcium levels. Moreover, Parathyroid hormone (PTH) and vitamin D levels will be evaluated as will be CBC, routine blood chemistry and metabolic profiles. Periodic physical and routine medical examination and a simple daily quality of life questionnaire will also be obtained.

Vitamin D and PTH levels will be assessed by ELISA techniques. To ascertain the validity of the results, the serum samples collected will also be analyzed for 25-OH Vitamin $D_3$ and PTH with a conventional high-pressure liquid chromatography (HPLC) method.

Enzyme-Linked ImmunoSorbent Assay (ELISA). Levels of serum 25-OH Vitamin $D_3$ and PTH will be analyzed using ELISA kits from INVITROGEN (Carlsbad, Calif.) and BIO-COMPARE (Bensheim, Germany) respectively, according to the manufacturers' instruction. Briefly, 96-well polystyrene plates will be coated with 100 µl/well buffer containing 100 ng anti-human PTH and 25-OH Vitamin $D_3$ for 2 hours at 37° C. ELISA buffer (150 µl) without TWEEN 20 is added and incubated for 2 hours at 37° C. to block non-specific binding. Fifty µl samples of purified anti-human PTH and 25-OH Vitamin $D_3$ for a calibration curve or 50 µl samples of serum samples will be added to each well, followed by 50 µl mouse monoclonal antiserum against PTH and 25-OH Vitamin $D_3$. The plates will be incubated overnight at 4° C. to reach equilibrium. Peroxidase-conjugated sheep anti-mouse antibody (50 µl/well; diluted 1:500) is added and incubated for 2 hours at room temperature. Addition of 100 µl Chromogen TMB buffer (Tetramethylbenzidine) yields a color reaction. The reaction is terminated by addition of 100 µl/well 1.0 NHCL, and after 5 minutes the absorbance is determined in an enzyme immunoassay plate reader (Dynex Technologies).

High Performance Liquid Chromatography (HPLC) Analyses. To 0.5 ml of serum is added 350 µl of methanol-2-propanol (80:20 by volume). The tubes will be mixed in a vortex mixer for 30 seconds. 25 (OH) Vitamin $D_3$ is extracted by mixing three times (60 seconds each time) with 2 ml of hexane. The phases will be separated by centrifugation, and the upper organic phase is transferred to a conical tube and dried under nitrogen. The residue is dissolved in 100 µl of mobile phase. Calibration curves will be constructed using different concentrations of 25(OH) $D_3$ (15-120 nmol/l) and human serum albumin (50 g/l).

For chromatography, a Beckman Coulter System Gold 125 solvent module HPLC system with a quaternary pump will be used. Separation will be performed on a PHENOMENEX column (150×4.60 mm; 5 micron) maintained at 40° C. The mobile phase will be 760 ml/1 methanol in water, and the flow rate will be 1 ml/min. UV/Fluorescence detection (variable wavelength detectors; Beckman Coulter) will be at 265 nm, and the injected volume will be 50 µl. The peak areas of the endogenous analyte will be subtracted from the supplemented sera before comparison. To clearly separate all of the peaks with the mobile phase used, a column 250 mm in length will be used.

All tests will be analyzed using Repeated Measure ANOVA to evaluate if there is any significant difference in impact of the study intervention during administration and withdrawal across the treatment period. A group analysis using paired t-test and between group analysis using two-sample t-test will be carried out to analyze any significant changes.

Clinical assessment will be evaluated using Quality of Life (QOL) index. The Quality of life data collected across visits will be analyzed within group using Wilcox sign rank test and between groups using Mann Whitney U test at the time periods for efficacy analysis.

Safety analysis will be carried out in the safety population defined above. Adverse events will be analyzed to evaluate the safety of the phosphate binder formulation in all patients receiving at least one dose of the study treatment.

All statistical tests will be performed at 95% significance level. Categorical data will be compared between test and control groups using Fisher's exact test.

Results of this analysis are expected to clearly demonstration that of sustained-release and enteric-coating increase efficacy of $CaCO_3$ as a phosphate binder in comparison to the non-coated form. It is expected that the enteric-coated, sustained-release calcium carbonate will reduce or stabilize hyperphosphatemic levels to normal levels preferably below 2.5 mg/dl.

What is claimed is:

1. A composition consisting of enteric-coated, sustained-release calcium carbonate.

2. The composition of claim 1, wherein the calcium carbonate is microcrystalline calcium carbonate.

3. The composition of claim 1, wherein said composition contains from 400 mg to 1500 mg of calcium.

4. A method for providing sustained-release of calcium carbonate in the small intestine of a subject comprising administering a composition of claim 1 to a subject in need thereof thereby providing sustained-release of calcium carbonate in the small intestine of the subject.

5. A method for inhibiting gastrointestinal absorption of phosphate in a subject comprising orally administering to a subject in need thereof an effective amount of the composition of claim 1 thereby inhibiting gastrointestinal absorption of phosphate in the subject.

6. A method for preventing or treating hyperphosphatemia comprising administering to a subject in need of treatment an effective amount of the composition of claim 1 thereby preventing or treating hyperphosphatemia in the subject.

* * * * *